(12) United States Patent
Barbieri et al.

(10) Patent No.: US 9,272,071 B2
(45) Date of Patent: Mar. 1, 2016

(54) OSTEOINDUCTIVE NANOCOMPOSITES (75) Inventors: Davide Barbieri, Utrecht (NL); Huipin Yuan, Zeist (NL); Joost Dick De Bruijn, Amersfoort (NL)

(73) Assignee: REVISIOS B.V. I.O., Bilthoven (NL)

( * ) Notice: Subject to any disclaimer, the term of this patent is extended or adjusted under 35 U.S.C. 154(b) by 1308 days.

(21) Appl. No.: 12/994,933

(22) PCT Filed: May 27, 2009

(86) PCT No.: PCT/NL2009/050296
§ 371 (c)(1),
(2), (4) Date: Jan. 6, 2011

(87) PCT Pub. No.: WO2009/145630
PCT Pub. Date: Dec. 3, 2009

(65) Prior Publication Data
US 2011/0111004 A1   May 12, 2011

(30) Foreign Application Priority Data

May 27, 2008 (EP) ..................................... 08157009

(51) Int. Cl.
*A61L 27/46* (2006.01)
(52) U.S. Cl.
CPC ............. *A61L 27/46* (2013.01); *A61L 2400/12* (2013.01)
(58) Field of Classification Search
None
See application file for complete search history.

(56) References Cited

U.S. PATENT DOCUMENTS

| 2002/0018797 A1* | 2/2002 | Cui et al. ....................... 424/423 |
| 2002/0115742 A1* | 8/2002 | Trieu et al. .................... 523/113 |
| 2003/0078317 A1* | 4/2003 | Lin et al. ....................... 523/116 |

(Continued)

FOREIGN PATENT DOCUMENTS

| EP | 1520593 | 4/2005 |
| WO | 2007103372 | 9/2007 |

OTHER PUBLICATIONS

International Preliminary Report on Patentability, Application No. PCT/NL2009/050296, mailed Jun. 16, 2010.

(Continued)

*Primary Examiner* — Ernst V Arnold
*Assistant Examiner* — Kyung Sook Chang
(74) *Attorney, Agent, or Firm* — Renner, Otto, Boisselle & Sklar, LLP (57) ABSTRACT

The present invention relates porous osteoinductive nanocomposites and for the methods to prepare osteoinductive nanocomposites. The osteoinductive composites consist of biocompatible polymers and non-heated (or non-sintered), needle-shaped or plate-like calcium phosphate nanocrystals and the methods comprise the steps of: a. adding phosphate to a calcium solution thereby evoking precipitation of calcium phosphate nanocrystals; b. washing the nanocrystals with water and suspending them in an organic solvent or getting dry calcium phosphate nanocrystals after evaporating organic solvent; c. adding polymers (previously dissolved in an organic solvent) to calcium phosphate nanocrystal suspension, rotational mixing of the components using beads, mixing with porogenic agents, moulding the composite material and evaporating of the organic solvent; or mixing polymers (not dissolved in an organic solvent but raw powder), dry calcium phosphate nanocrystals and porogenic agents with melting intrusion and moulding the composites; d. leaching porogenic agents in water.

19 Claims, 4 Drawing Sheets (56) References Cited

U.S. PATENT DOCUMENTS

2003/0180344 A1 9/2003 Wise et al.
2007/0156238 A1 7/2007 Liao et al.

OTHER PUBLICATIONS

International Search Report, Application No. PCT/NL2009/050296, mailed Jul. 15, 2009.

* cited by examiner

OSTEOINDUCTIVE NANOCOMPOSITES

FIELD OF THE INVENTION

The invention relates to porous osteoinductive nanocomposite materials and to methods of producing these materials.

BACKGROUND OF THE INVENTION

Autologous bone harvested from the patient's own bone is the gold standard bone substitute for repairing large bone defects. However, the amount of autologous bone harvestable from a patient is limited and the bone subtraction itself poses significant health risks and results in loss of structural integrity of the remaining bone.

Developments in tissue engineering have provided synthetic implants, for instance in the form of scaffold materials, which allow attachment of bone cells and ingrowth of new bone tissue and subsequent deposition of new bone mineral. The synthetic materials may either be grafted ex vivo with bone cells prior to implantation or may be implanted as naked scaffolds that attract bone cells from the periphery to the site of the implant.

Recent advances in tissue engineering have produced a variety of valuable scaffold materials. Calcium phosphates such as hydroxyapatite (HA; the mineral phase of bone), biphasic calcium phosphate (BCP) and α- or β-tricalcium phosphate (TCP) are known to possess both osteoconductive (bioactive) as well as osteoinductive properties and provide very suitable scaffold materials. The bioactive nature of calcium phosphates allows them to function as a template for new bone formation by osteogenic cells through deposition of new mineral material at the scaffold's surface and is an important feature of the scaffold material. The osteoinductive nature of calcium phosphates is a qualitative feature, i.e. the capacity to induce the development of the new bone tissue, thereby enhancing the rate of deposition of new mineral, depends on various material parameters. Bone induction is generally defined as the mechanism by which a mesenchymal tissue is induced to change its cellular structure to become osteogenic. Bone formation in scaffolding materials following ectopic implantation (i.e. intramuscular implantation or subcutaneous implantation) is generally a demonstration of osteoinduction of such scaffolding materials.

In general, porous calcium phosphates have been found to exhibit osteoinductivity. For instance, Yamasaki et al., in Biomaterials 13:308-312 (1992), describe the occurrence of heterotopic ossification (formation of new bone in tissue that does not normally ossify) around porous hydroxyapatite ceramic granules, but not around dense granules. The porous granules range in size from 200 to 600 μm, and have a continuous and interconnected microporosity of which the pores range in diameter from 2 to 10 μm.

At present there still exists a need for additional composite materials with osteoinductive properties.

SUMMARY OF THE INVENTION

The present invention describes porous osteoinductive nanocomposites and the methods to make such porous osteoinductive nanocomposites.
  a. the said porous composites comprise, preferably consist of, biocompatible polymers and amorphous non-stoichiometric calcium phosphate nanocrystals;
  b. the said calcium phosphate nanocrystals are not heated or sintered at above 100° C.;
  c. in said porous composites the content of said calcium phosphate nanocrystals is above 20% by weight;
  d. the said porous composites are porous with pores larger than 50 μm;
  e. the said porous composites have porosity over than 10%.

In a first aspect, the present invention provides a porous osteoinductive composite material comprising a biocompatible polymer, at least 20 wt. %, based on the weight of the total composition, of calcium phosphate nanocrystals, said composite having a porosity of at least 10% and having pores with a pore size of at least 50 μm.

In a preferred embodiment of a material of the present invention, said calcium phosphate nanocrystals are non-heated or non-sintered amorphous non-stoichiometric calcium phosphate crystals.

In a preferred embodiment of a material of the present invention, said calcium phosphate nanocrystals have needle-shaped or plate-like crystals having a width of about 5-200 nm, preferably about 10-150 nm.

In a preferred embodiment of a material of the present invention, said calcium phosphate nanocrystals have needle-shaped or plate-like crystals of which the length is not particularly limiting.

The present invention thus inter alia provides a porous osteoinductive nanocomposites and for the methods to prepare osteoinductive nanocomposites. The osteoinductive composites consist of biocompatible polymers and non-heated (or non-sintered), needle-shaped or plate-like calcium phosphate nanocrystals and the methods preferably comprise the steps of: a. adding phosphate to a calcium solution thereby evoking precipitation of calcium phosphate nanocrystals; b. washing the nanocrystals with water and suspending them in an organic solvent or getting dry calcium phosphate nanocrystals after evaporating organic solvent; c. adding polymers (previously dissolved in an organic solvent) to calcium phosphate nanocrystal suspension, rotational mixing of the components using beads, mixing with porogenic agents, moulding the composite material and evaporating of the organic solvent; or mixing polymers (not dissolved in an organic solvent but raw powder), dry calcium phosphate nanocrystals and porogenic agents with melting intrusion and moulding the composites; d. leaching porogenic agents in water.

In a preferred embodiment of a material of the present invention, said calcium phosphate nanocrystals are present in said material in an amount of at least 20 wt. %, preferably at least 40 wt. %;

In a preferred embodiment of a material of the present invention, said porosity is 30 to 70% and wherein said pore size is 100 to 1000 μm.

In another aspect, the present invention provides a method for preparing an osteoinductive composite material, comprising the steps of:
a) adding phosphate to a calcium solution thereby evoking precipitation of calcium phosphate nanocrystals;
b) washing the calcium phosphate nanocrystals with water and either suspending the nanocrystals in an organic solvent to provide a suspension of calcium phosphate nanocrystals and/or drying said calcium phosphate nanocrystals by evaporating said organic solvent to provide powder of dried calcium phosphate nanocrystals;
c) providing a polymer in the form of a polymer solution wherein said polymer is dissolved in an organic solvent capable of dissolving said polymer or providing a meltable polymer in the form of a dry powder;
d) mixing the calcium phosphate nanocrystals of step b) with the polymer provided in step c), in order to provide a composite mixture, preferably said mixing is performed by rotational mixing, preferably using beads, to provide a composite material mixture;

e) adding a porogenic agent to said composite material mixture and continue mixing to provide a composite material mixture with porogenic agent, in the form of a melt prepared by melting intrusion of the dry components or in the form of a solution prepared by mixing the dissolved and/or suspended components;

f) moulding the composite material mixture with porogenic agent by pouring the said composite material mixture with porogenic agent into a mould and evaporating the organic solvent, or by cooling said melt of said composite material mixture with porogenic agent and allowing it to set, thereby providing a moulded composite material mixture with porogenic agent;

g) leaching the porogenic agent from the said moulded composite material mixture with porogenic agent by contacting said porogenic agent with a suitable solvent, preferably water.

The skilled person will understand that the material may also be moulded after setting of the composite, for instance by milling or by cutting, into a desired shape. In such instances, the moulded composite of the present invention may take any shape desirable.

In a preferred embodiment of a method of the present invention, the calcium phosphate nanocrystals are prepared using a calcium solution comprising not more than 0.5M of Ca, and a phosphate solution comprising not more than 0.5M of P at a reaction rate equivalent to the production of 1 gram of nanocrystals per minute.

In another preferred embodiment of a method of the present invention, the dry calcium phosphate nanocrystals are obtained through dehydration with organic agents, such as acetone and ethanol.

In another preferred embodiment of a method of the present invention, wherein the polymer in step c) is dissolved in the same organic solvent as used for the calcium phosphate in step b).

In another preferred embodiment of a method of the present invention, said porogenic agent is in the form of particles selected from the group consisting of salts (NaCl, KCl, $CaCl_2$, sodium tartrate, sodium citrate and the like), biocompatible mono- and disaccharides (glucose, fructose, dextrose, maltose, lactose, sucrose), polysaccharides (starch, alginate, pectin) and water soluble proteins (gelatine, agarose), more preferably wherein said porogenic agent is NaCl.

In another preferred embodiment of a method of the present invention, the organic solvent is chosen from the group consisting of ethanol, ethyl formate, hexafluoro-2-propanol (HFIP), cyclic ethers (i.e. tetrahydrofuran (THF), and 2,5-dimethylfuran (DMF)), acetone, acetates of C2 to C5 alcohol (such as ethyl acetate and butyl acetate), glyme or dimethoxyethane (i.e. monoglyme, ethyl glyme, diglyme, ethyl diglyme, triglyme, butyl diglyme, tetraglyme, dimethyl glycol, ethylene glycol dimethyl ether, dimethyl cellosolve, and DME), methylethyl ketone (i.e. butanone), dipropyleneglycol methyl ether, lactones (such as δ-valerolactone, γ-valerolactone, b-butyrolactone, g-butyrolactone), 1,4-dioxane, 1,3-dioxolane, ethylene carbonate, dimethylcarbonate, diethylcarbonate, benzene, toluene, benzyl alcohol, p-xylene, N-methyl-2-pyrrolidone, dimethylformamide, chloroform (i.e. trichloromethane, methyl trichloride), 1,2-dichloromethane (DCM), morpholine, dimethylsulfoxide (DMSO), hexafluoroacetone sesquihydrate (HFAS), anisole (i.e. methoxybenzene) and mixtures thereof.

In another preferred embodiment of a method of the present invention, the organic solvent is acetone.

In another preferred embodiment of a method of the present invention, the polymer is chosen from the group consisting of polyesters (polylactide (PLA), polyglycolide (PGA), copolymers of PLA and PGA, polycaprolactone (PCL) and copolymers based on PCL, polyanhydrides, polyamides, polyurethanes, polyesteramides, polyorthoesters, polydioxanones, polyacetals, polyketals, polycarbonates, polyphosphazenes, polyhydroxybutyrates, polyhydroxyvalerates, polyalkylee oxalates, polyalkylene succinates, poly (malic acid), poly(amino acids), poly(methylvinyl ether), poly(maleic anhydride), polyvinyl alcohol, and copolymers, terpolymers, natural polymers such as celluloses (i.e. hydroxymethyl cellulose, carboxymethyl cellulose, hydroxypropylmethyl cellulose), chitosan, alginate, collagen, chitin, glycogen, starch, keratins, polypepetides or combinations or mixtures thereof.

In another preferred embodiment of a method of the present invention, wherein the polymer is chosen from PLA, PCL or copolymers thereof.

In another preferred embodiment of a method of the present invention as described above, wherein the calcium phosphate is in the form of amorphous non-stoichiometric calcium phosphate nano-crystals with Ca/P ratio of 1.0-2.0, preferably 1.50 to 1.67 and more preferably 1.67.

In another preferred embodiment of a method of the present invention as described above, for preparing a material according to the present invention as described above.

In another aspect, the present invention provides an osteoinductive composite according to the present invention as described above, produced by the methods according to the present invention as described above.

In another aspect, the present invention provides the use of the osteoinductive composite material according to the present invention as described above for the induction of bone formation in a living organism.

In another aspect, the present invention provides the use of the osteoinductive composite material according to the present invention as described above as an implant material alone or combined with growth factors or/and cells for the production of autologous bone in a non-osseous site.

In another aspect, the present invention provides the use of the osteoinductive composite material according to the present invention as described above for the production of a medical implant or device alone or combined with growth factors or/and cells.

Uses of the invention are particularly beneficial in dental surgery and/or for the reconstruction of bone The term "amorphous non-stoichiometric calcium phosphate nanocrystals" is used to refer to non-hydroxyl apatite (HA) materials, which are typically sintered (heated) materials wherein the crystals are aligned, in stead of the random crystals obtained in amorphous crystals. Hence in a process of the invention the calcium phosphate is obtained preferably through precipitation at temperatures below 100° C., preferably below 80° C. The composite then has as a feature that it exhibits high mechanical strength, it is bioactive, bone bonding, and may show resorption of the CaP part in vivo.

One of said methods for the production of the nanocomposite of the present invention may comprise the steps of:

a. adding phosphate to a calcium solution thereby evoking precipitation of nano-scaled amorphous non-stoichiometric calcium phosphate crystals, optionally washing calcium phosphate crystals, preferably with distilled water, optionally filter or sieve to selected size range;

b. suspending them in an organic solvent;

c. adding a polymer (previously dissolved in an organic solvent);
d. mixing the components, preferably by rotational mixing using beads;
e. adding porogenic agents to the composites and uniformly mix;
f. optionally moulding the composite material;
g. evaporation of the organic solvent; and
h. leaching the porogenic agents in water.

Preferably in said method the polymer is solved in the same organic solvent used in step b.

Alternatively said method can also comprise:
a. adding phosphate to a calcium solution thereby evoking precipitation of nano-scaled amorphous non-stoichiometric calcium phosphate crystals;
b. washing calcium phosphate crystals with distilled water, filter and dehydrate with an organic solvent;
c. evaporating organic solvent to get dry calcium phosphate nano-crystals;
d. mixing polymer, dry calcium phosphate nano-crystals and porogenic agents with melting intrusion;
e. optionally moulding the composite material; and
f. leaching the porogenic agents in water.

In said method, in step b., the amorphous non-stoichiometric calcium phosphate crystals can suitably be dried through vacuum filtration in order to get a cake of calcium phosphate crystals.

In said method, in step b., the cake of calcium phosphate crystals can be dehydrated by washing the cake with an organic solvent (preferably at least 10 times).

The solvent used for dehydration can be then removed from the calcium phosphate nanocrystals by evaporating the organic solvent at a temperature between room temperature and 100° C., more preferably between 50 and 100° C.

In said method, in step d., the raw powder of polymer (not dissolved in the organic solvent), the said dry calcium phosphate nanocrystals and the porogenic agent are heated at a high enough temperature to melt the polymer and mix the three components together (melting intrusion).

In a further preferred embodiment a porogenic agent is added while mixing, preferably wherein said porogenic agent is chosen from the group consisting of salts (NaCl, KCl, $CaCl_2$, sodium tartrate, sodium citrate and the like), biocompatible mono- and disaccharides (glucose, fructose, dextrose, maltose, lactose, sucrose), polysaccharides (starch, alginate, pectin) and water soluble proteins (gelatine, agarose), more preferably said porogenic agent is NaCl.

In the method of the invention the crystals of the sodium chloride preferably have a particle size of about 100-600, more preferably about 200-500 μm, still more preferably about 300-400 μm.

The organic solvent is chosen from the group consisting of ethanol, ethyl formate, hexafluoro-2-propanol (HFIP), cyclic ethers (i.e. tetrahydrofuran (THF), and 2,5-dimethylfuran (DMF)), acetone, acetates of C2 to C5 alcohol (such as ethyl acetate and butyl acetate), glyme or dimethoxyethane (i.e. monoglyme, ethyl glyme, diglyme, ethyl diglyme, triglyme, butyl diglyme, tetraglyme, dimethyl glycol, ethylene glycol dimethyl ether, dimethyl cellosolve, and DME), methylethyl ketone (i.e. butanone), dipropyleneglycol methyl ether, lactones (such as ε-valerolactone, γ-valerolactone, b-butyrolactone, g-butyrolactone), 1,4-dioxane, 1,3-dioxolane, ethylene carbonate, dimethylcarbonate, diethylcarbonate, benzene, toluene, benzyl alcohol, p-xylene, N-methyl-2-pyrrolidone, dimethylformamide, chloroform (i.e. trichloromethane, methyl trichloride), 1,2-dichloromethane (DCM), morpholine, dimethylsulfoxide, hexafluoroacetone sesquihydrate (HFAS), anisole (i.e. methoxybenzene) and mixtures thereof and preferably the organic solvent is acetone.

The polymer is preferably chosen from the group consisting of polyesters, polylactic acid or polylactide (PLA), polyglycolide (PGA), copolymers of PLA and PGA, polycaprolactone (PCL) and copolymers based on PCL, polyanhydrides, polyamides, polyurethanes, polyesteramides, polyorthoesters, polydioxanones, polyacetals, polyketals, polycarbonates, polyphosphazenes, polyhydroxybutyrates, polyhydroxyvalerates, polyalkylee oxalates, polyalkylene succinates, poly(malic acid), poly(amino acids), poly(methylvinyl ether), poly(maleic anhydride), polyvinyl alcohol, and copolymers, terpolymers, natural polymers such as celluloses (i.e. hydroxymethyl cellulose, carboxymethyl cellulose, hydroxypropylmethyl cellulose), chitosan, alginate, collagen, chitin, glycogen, starch, keratins, polypepetides or combinations or mixtures thereof and preferably the polymer is chosen from PLA, PCL or copolymers thereof.

The calcium phosphate is in the form of amorphous non-stoichiometric nano-crystals with Ca/P ratio of 1.0 to 2.0 preferably with a Ca/P ratio of 1.67.

The calcium phosphate is not a hydroxyapatite, with which is meant that produced by heating, i.e. that it is not a sintered (heated to >900° C.) calcium phosphate and also not a calcined (heated to between 100-900° C.) calcium phosphate, and that the crustal structure is amourphous.

In the method of the invention the crystals of the calcium phosphate (the CaP nanocrystals) preferably have a width of about 5-200 nm, more preferably about 10-150 nm. The length of the crystals is not particularly limited. The content in apatite of said composite is higher than 20% (by weight of the composite), more preferably higher than 40% (by weight of the composite).

In another embodiment, the invention comprises an osteoinductive composite material produced by the methods according to the invention. The material of the present invention is characterized in that it exhibits osteoinductive capacity, meaning that when a culture of osteoblastic cells is exposed to the material, the cells will express alkaline phosphatase activity and form bone apatite.

A further part of the invention is the use of said osteoinductive composite material for the induction of bone formation ectopically in a living organism. Alternatively the osteoinductive composite material according to the invention is used as an implant material alone or combined with growth factors or/and cells for the production of autologous bone in a non-osseous site. In such a way the osteoinductive composite material according to the invention can be used for the production of a medical implant or device alone or combined with growth factors or/and cells. One of the areas where such an osteoinductive composite material can be applied is the field of dentistry.

DETAILED DESCRIPTION OF THE INVENTION

A calcium phosphate material or calcium phosphate composite in aspects of the present invention may be based on any calcium phosphate (CaP), such as a CaP obtained by precipitation from an aqueous solution at low temperature (e.g. 20-80° C.) or by a high temperature (thermal) process (but preferably not higher than 100° C. Highly preferred calcium phosphates are the calcium orthophosphates. The term "calcium orthophosphate" as used herein refers to a family of compounds, each of which contains a calcium cation, $Ca^{2+}$, and a phosphate anion, $PO_4^{3-}$. Under this definition, there are multiple calcium orthophosphates, including monocalcium orthophosphate (monobasic), dicalcium orthophosphate (dibasic), tricalcium orthophosphate (tribasic), and hydroxyapatite (penta calcium triphosphate).

Although this invention is described mainly in terms of calcium orthophosphate, other suitable materials useful herein include for instance calcium pyrophosphates dicalcium diphosphate ($Ca_2P_2O_7$, synonym: calcium pyrophosphate), calcium pyrophosphate dihydrate (CPPD, $Ca_2P_2O_7.2H_2O$), and calcium dihydrogen diphosphate ($CaH_2P_2O_7$; synonyms: acid calcium pyrophosphate, monocalcium dihydrogen pyrophosphate)), and polyphosphate (($CaP_2O_6$)$_n$, n≥2; synonyms: calcium metaphosphates, calcium polymetaphosphates), and combinations of the various phosphates.

Non-limiting examples of the calcium phosphate compound that may be used in aspects of the invention are:
- amorphous calcium phosphate (ACP, $Ca_3(PO_4)_2.nH_2O$, n=3-4.5, Ca/P ratio=1.5)
- apatite (calcium fluoro-phosphate, $Ca_5(F,Cl,OH)(PO_4)_3$)
- calcium dihydrogen phosphate ($Ca(H_2PO_4)_2$);
- calcium dihydrogen phosphate hydrate ($Ca(H_2PO_4)_2.H_2O$)
- calcium hydrogen phosphate hydrate ($CaHPO_4.2H_2O$);
- calcium hydrogen phosphate, anhydrous ($CaHPO_4$),
- calcium-deficient hydroxyapatite or precipitated hydroxyapatite (PHA) $Ca_{10-x}(HPO_4)_x(PO_4)_{6-x}(OH)_{2-x}$ (0≤x≤1) with Ca/P ratio varying from 1.5 to 1.67
- carbonate apatite ($Ca_5(PO_4,CO_3)_3F$)
- dicalcium phosphate anhydrous (DCPA, $CaHPO_4$)
- dicalcium phosphate dihydrate (DCPD, $CaHPO_4.2H_2O$);
- monocalcium phosphate anhydrous (MCPA, $Ca(H_2PO_4)_2$);
- monocalcium phosphate monohydrate (MCPM, $Ca(H_2PO_4)_2.H_2O$);
- octacalcium phosphate (OCP, $Ca_8H_2(PO_4)6.5H_2O$);
- mixtures of two or more of the above such as mixtures of MCPM or MCPA with another CaP, and
- composites of two or more of the above having Ca/P ratio of 1.0-2.0.

The calcium phosphates used in methods of the present invention are nanocrystals and are preferably obtained by precipitation from a solution comprising suitable calcium and phosphate sources. The skilled person is well aware that precipitation of calcium phosphates from such a solution will occur depending on the pH of the solution. Suitably the precipitation occurs in the presence of a base. A suitable calcium source is $Ca(NO_3)_2.4H_2O$. A suitable phosphate source is $(NH_4)_2HPO_4$. As a base, ammonia may be used.

Additionally, calcium phosphates nanocrystals may be obtained by other methods, such as by milling and/or sieving of calcium phosphates microparticles. However, the preparation of calcium phosphates nanocrystals by precipitation is most preferred.

The calcium phosphates, particularly in case they are derived from natural sources, may be calcined prior to use as used in most of the applications. Preparation of osteoinductive material of the invention which preferably used as an implant in living tissue should mimic the way by which living organs produce mineralized tissues, the calcium phosphate is therefore preferably not sintered or heated. Moreover, the osteoinductive material is preferably both sufficiently compatible and sufficiently biodegradable for use as an implant in living tissue. Thus, the calcium phosphate on which the osteoinductive material is based is preferably (bio)resorbable, meaning that it exhibits chemical dissolution and cell-mediated resorption when placed in a mammalian body.

An osteoinductive material according to the invention is preferably based on any calcium phosphates having Ca/P ration of 1.0-2.0 or combinations thereof. An osteoinductive material according to the invention is most preferably based on a calcium phosphate having Ca/P ratio of 1.50 to 1.67.

Synthetic polymers provide for very suitable organic scaffold materials. Advantages of such polymers include the ability to tailor mechanical properties and degradation kinetics to suit various applications. Synthetic polymers are also attractive because they can be fabricated into various shapes with desired pore morphologic features conducive to tissue in-growth. Furthermore, polymers can be designed with chemical functional groups that can induce tissue in-growth. Numerous synthetic polymers can be used to prepare synthetic polymer-comprising scaffolds useful in methods of the invention. They may be obtained from sources such as Sigma Chemical Co., St. Louis, Mo., Polysciences, Warrenton, Pa., Aldrich, Milwaukee, Wis., Fluka, Ronkonkoma, N.Y., and BioRad, Richmond, Calif.

Representative synthetic polymers include alkyl cellulose, cellulose esters, cellulose ethers, hydroxyalkyl celluloses, nitrocelluloses, polyalkylene glycols, polyalkylene oxides, polyalkylene terephthalates, polyalkylenes, polyamides, polyanhydrides, polycarbonates, polyesters, polyglycolides, polymers of acrylic and methacrylic esters, polyorthoesters, polyphosphazenes, polysiloxanes, polyurethanes, polyvinyl alcohols, polyvinyl esters, polyvinyl ethers, polyvinyl halides, polyvinylpyrrolidone, and blends and copolymers of the above. The scaffold may comprise both oligomers and polymers of the above.

Specific examples of these broad classes of polymers include poly(methyl methacrylate), poly(ethyl methacrylate), poly(butyl methacrylate), poly(isobutyl methacrylate), poly(hexyl methacrylate), poly(isodecyl methacrylate), poly (lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate), poly (vinyl chloride), polystyrene, polyurethane, poly(lactic acid), poly(butyric acid), poly(valeric acid), poly[lactide-co-glycolide], poly(fumaric acid), poly(maleic acid), copolymers of poly (caprolactone) or poly (lactic acid) with polyethylene glycol and blends thereof.

The polymers used in scaffolds may be non-biodegradable. Examples of preferred non-biodegradable polymers include ethylene vinyl acetate, poly(meth)acrylic acid, polyamides, and copolymers and mixtures thereof.

Polymers used in scaffolds may also be biodegradable. For a detailed review on biodegradable synthetic polymers for tissue engineering, reference is made to the publication by Gunatillake and Adhikari in Cell (Gunatillake A., Adhikari, 2003). The rate of degradation of the biodegradable scaffolds is determined by factors such as configurational structure, copolymer ratio, crystallinity, molecular weight, morphology, stresses, amount of residual monomer, porosity and site of implantation. The skilled person will be able to choose the combination of factors and characteristics such that the rate of degradation is optimized.

Examples of preferred biodegradable polymers include synthetic polymers such as polyesters, polyanhydrides, poly(ortho)esters, polyurethanes, siloxane-based polyurethanes, poly(butyric acid), tyrosine-based polycarbonates, and natural polymers and polymers derived therefrom such as albumin, alginate, casein, chitin, chitosan, collagen, dextran, elastin, proteoglycans, gelatin and other hydrophilic proteins, glutin, zein and other prolamines and hydrophobic proteins, starch and other polysaccharides including cellulose and derivatives thereof (e.g. methyl cellulose, ethyl cellulose, hydroxypropyl cellulose, hydroxy-propyl methyl cellulose, hydroxybutyl methyl cellulose, carboxymethyl cellulose, cellulose acetate, cellulose propionate, cellulose acetate butyrate, cellulose acetate phthalate, cellulose acetate succinate, hydroxypropylmethylcellulose phthalate, cellulose triacetate, cellulose sulphate), poly-1-lysine, polyethylenimine, poly(alkyl amine), polyhyaluronic acids, and combinations, copolymers, mixtures and chemical derivatives thereof (substitutions, additions of chemical groups, for example, alkyl, alkylene, hydroxylations, oxidations, and other modifications routinely made by those skilled in the art). In general, these materials degrade either by enzymatic hydrolysis or exposure to water in vivo, by surface or bulk erosion.

The foregoing materials may be used alone, as physical mixtures (blends), or as a co-polymer. The most preferred polymers are polyesters, polyanhydrides, polystyrenes and blends thereof. The polyesters and polyanhydrides are advantageous due to their ease of degradation by hydrolysis of ester linkage, degradation products being resorbed through the metabolic pathways of the body in some cases and because of their potential to tailor the structure to alter degradation rates. Some disadvantages of these polymers in prior art tissue engineering applications are their release of acidic degradation products and its effect on the regenerating tissue. By using a method of the present invention, this disadvantage is essentially overcome. The mechanical properties of the biodegradable material are preferably selected such that early degradation, i.e. degradation prior to sufficient regeneration of the desired tissue, and concomitant loss of mechanical strength is prevented.

Preferred biodegradable polyesters are for instance poly(glycolic acid) (PGA), poly(lactic acid) (PLA), poly(glycolic-co-lactic acid) (PGLA), poly(dioxanone), poly(caprolactone) (PCL), poly(3-hydroxybutyrate) (PHB), poly(3-hydroxyvalerate) (PHV), poly(lactide-co-caprolactone) (PLCL), poly(valerolactone) (PVL), poly(tartronic acid), poly($\beta$-malonic acid), poly(propylene fumarate) (PPF) (preferably photo cross-linkable), poly(ethylene glycol)/poly(lactic acid) (PELA) block copolymer, poly(L-lactic acid-ϵ-caprolactone) copolymer, and poly(lactide)-poly(ethylene glycol) copolymers.

Preferred biodegradable polyanhydrides are for instance poly[1,6-bis(carboxyphenoxy)hexane], poly(fumaric-co-sebacic)acid or P(FA:SA), and such polyanhydrides may be used in the form of copolymers with polyimides or poly(anhydrides-co-imides) such as poly-[trimellitylimidoglycine-co-bis(carboxyphenoxy)hexane], poly[pyromellitylimidoalanine-co-1,6-bis(carboph-enoxy)-hexane], poly[sebacic acid-co-1,6-bis(p-carboxyphenoxy)hexane] or P(SA:CPH) and poly[sebacic acid-co-1,3-bis(p-carboxyphenoxy)propane] or P(SA:CPP). Poly(anhydride-co-imides) have significantly improved mechanical properties over poly-anhydrides, particularly compressive strengths. Particularly preferred are photo cross-linkable polyanhydrides and copolymers thereof.

Other suitable scaffold materials are biocompatible materials that are accepted by the tissue surface. The broad term biocompatible includes also nontoxicity, noncarcinogenity, chemical inertness, and stability of the material in the living body. Exemplary biocompatible materials are titanium, alumina, zirconia, stainless steel, cobalt and alloys thereof and ceramic materials derived thereform such as $ZrO_2$ and/or $Al_2O_3$. Almost all metallic implants and ceramics are bioinert, meaning that a dense fibrous tissue of variable thickness will encapsulate the scaffold, which prevents proper distribution of stresses and may cause loosening of the implant. Therefore, in specific applications bioactive materials are preferably used. Such materials result in the formation of an interfacial bond between the scaffold and the surrounding tissue.

As examples of inorganic scaffold materials calcium phosphate matrices (CaP) and hydroxyapatite (HA) matrices may be used. CaP, sintered hydroxyapatite and bioactive glasses or ceramics, such as 45S5 Bioglass® (US Biomaterials Corp, USA), and apatite- and wollastonite-containing glass-ceramic (glass-ceramic A-W), that form bone-like apatite on their surfaces in the living body and thereby bond to the living bone, exhibit high bioactivity and biocompatibility and are therefore also very suitable for use in the present invention. Hydroxyapatite has the advantage that it is osteoconductive, which term refers to the materials ability to guide bone formation and bond to bone. A subclass of calcium phosphates which comprise specific arrangements of surface microporosity and micro-architecture have been described as being osteoinductive, which term refers to the materials ability to induce bone cell growth. Very suitable matrix materials are the combined materials such as osteoinductive hydroxyapatite/tricalcium phosphate (HA/TCP) matrices, preferably biphasic calcium phosphate (BCP).

A disadvantage of these inorganic and ceramic materials is that they are in principle brittle and hence primarily find their application in non-load bearing functions. Such materials may be combined with polymers in order to produce a composite with mechanical properties analogous to bone and a bioactive character. Specifically suitable composite materials are for instance hydroxyapatite coatings on titanium-based implants, layered double hydroxide nanocomposites, HA reinforced with high-density polyethylene, plasma sprayed HA/ZrO2 composite coatings, oxide ceramics with calcium phosphate coatings, glass hydroxyapatite coatings on titanium, and polydimethylsiloxane (PDMS)-$TiO_2$ hybrid optionally treated with hot water.

All of the above scaffold materials may be used in different forms such as in the form of blocks, foams, sponges, granules, cements, implant coatings, composite components and may for instance be combined organic/inorganic materials or ceramics and may be from various origins, natural, biological or synthetic. The various forms may for instance be obtained by extrusion, injection moulding, solvent casting, particular leaching methods, compression moulding and rapid prototyping such as 3D Printing, Multi-phase Jet Solidification, and Fused Deposition Modeling (FDM) of the materials.

A suitable cement may for instance be used as a injectable (bone) scaffold material and may upon hardening and vascularization later be loaded with the cells. Such a cement may for instance comprise hydroxyapatite (HA) nanocrystals in combination with a curable polymer.

The scaffold will generally be implanted by surgery. The surgical procedures to implant the scaffold may be similar to the procedures that are normally used by the skilled surgeon when implanting other types of scaffolds.

The nanocomposite of the present invention may be porous or dense, but is preferably porous. Preferably the composite material is macroporous, with pore size ranging from 10-1000 μm, preferably of 50-500 μm, more preferably 3-400 μm. The total porosity may for instance range from 10 to 90%, preferably from 30 to 70%. Porosity can be achieved by the composite itself, but also by adding a porogenic compound when manufacturing the composite. Such porogenic compounds are salts (NaCl, KCl, $CaCl_2$, sodium tartrate, sodium citrate and the like), biocompatible mono- and disaccharides (glucose, fructose, dextrose, maltose, lactose, sucrose), polysaccharides (starch, alginate, pectin) and water soluble proteins (gelatine and agarose). Most preferably NaCl is used with a particle size of between about 50 μm to about 1000 μm.

The calcium phosphate nanocrystals of the present invention are preferably dense, needle-shaped or plate-like crystals.

The composite of the present invention is made by preparing a calcium phosphate slurry comprising nanocrystals of a calcium phosphate compound in a standard way e.g. using a wet-precipitation reaction at controlled pH and temperature using calcium nitrate tetrahydrate and diammonium hydrogen phosphate at a Ca/P ratio of 1.67. Other methods of preparing a nanosized calcium phosphate compound chosen from the group of compounds described above are within the skill of the person skilled in the art.

The thus obtained nanocrystals are dispersed in an organic solvent, which may be chosen from the group of ethanol, ethyl formate, hexafluoro-2-propanol (HFIP), cyclic ethers (i.e. tetrahydrofuran (THF), and 2,5-dimethylfuran (DMF)), acetone, acetates of C2 to C5 alcohol (such as ethyl acetate and butyl acetate), glyme or dimethoxyethane (i.e. monoglyme, ethyl glyme, diglyme, ethyl diglyme, triglyme, butyl diglyme, tetraglyme, dimethyl glycol, ethylene glycol dimethyl ether, dimethyl cellosolve, and DME), methylethyl ketone (i.e. butanone), dipropyleneglycol methyl ether, lactones (such as δ-valerolactone, γ-valerolactone, b-butyrolactone, g-butyrolactone), 1,4-dioxane, 1,3-dioxolane, ethylene carbonate, dimethylcarbonate, diethylcarbonate, benzene, toluene, benzyl alcohol, p-xylene, N-methyl-2-pyrrolidone, dimethylformamide, chloroform (i.e. trichloromethane, methyl trichloride), 1,2-dichloromethane (DCM), morpholine, dimethylsulfoxide, hexafluoroacetone sesquihydrate (HFAS), anisole (i.e. methoxybenzene) and mixtures thereof. Preferably the organic solvent is acetone. One of the advantages of acetone is that it has polar (—C=O) and non-polar (—$CH_3$) groups that enable it to dissolve almost all the polymers as mentioned above, but not the salts used a porogenic agent.

To this dispersion the polymer is added. The polymer can be in liquid or in powder form, but preferably is added as a solution or dispersion in the same organic solvent. Together with the polymer preferably also the porogenic agent is added.

While the individual concentrations of the nanocrystals and the polymer are only important for the thickness and ease of handling the mixture, the polymer and nanocrystals weight ratio is determining the characteristics of the composite that is formed. Thus, it is sufficient to dissolve the proper weight of polymer in a volume of solvent and mix this volume with a known volume of nanocrystals suspension (since the weight of the nanocrystals depends on the volume of the suspension). Then it is possible to add more solvent to increase the miscibility or workability of the composite slurry.

This mixture is mixed in a rotational mixer, such as a ball mill, using beads. Preferably, glass beads are used with a diameter ranging between 3-10 mm. The loading volume of the ball mill preferably is about ⅓ filled with the beads to ensure a proper mixing and homogenization of the composite. When the mixture is still in semi-liquid or liquid form, it is possible to mould the composition into predetermined shapes, like discs, blocks or whatever structure is needed. The composite structure is then formed by evaporating the organic solvent.

In this way, a composite is obtained, in which the nanocrystals are homogenously dispersed in the polymer. As is shown in the example in this way an excellent osteoinductive material can be obtained.

Alternatively, after the precipitation reaction and washing step with distilled water (preferably washing is continued until ammonia vapour is no longer discernable), the amorphous non-stoichiometric calcium phosphate crystals can be dried through vacuum filtration in order to provide a cake of calcium phosphate crystals.

The cake of calcium phosphate crystals can then be dehydrated by washing the cake with an organic solvent, suitably for at least 10 times.

The solvent used for dehydration can be removed from the calcium phosphate nanocrystals by evaporating the organic solvent at a temperature between room temperature and 100° C., more preferably between 50 and 100° C.

The raw powder of the polymer (not dissolved in the organic solvent), the dry powder of said calcium phosphate nanocrystals and the porogenic agent are heated at a sufficiently high temperature to melt the polymer and mix the three components together (melting intrusion).

The material of the present invention may be used as calcium phosphate cement or it may be used for inducing the formation of bone tissue in a living organism.

The material of the present invention may suitably be used as an implant material, i.e. as a scaffold, for the production of autologous bone in a non-osseous site. This ability is due to the highly osteoinductive properties of the material.

The material of the invention may thus be used as a medical implant or medical device formed of a calcium phosphate. It is also possible that the material is used in combination with a medical implant of a different material, such as a metal or a polymeric material, on which the osteoinductive material according to the invention is present in the form of a coating.

In another preferred embodiment, the mould can be in the form of a spinal cage where the composite material of the invention is injection moulded in this shape, or alternatively shaped into a spinal cage after setting of the composite.

In still another preferred embodiment of a method of the invention, said scaffold comprises angiogenese stimulating factors selected from the group consisting of angiomotin, vascular endothelial growth factor (VEGF), autotaxin [ATX (NPP-2)], epidermal growth factor (EGF), platelet-derived growth factors (PDGFs), Mts-1 protein; basic fibroblast growth factor (bFGF) or prostratropin; transforming growth factors (TGFs) and nitric oxide (NO). BMPs may also be incorporated into a scaffold to reproduce the tissue healing cascade at sites that are resistant to normal healing.

It is an advantage of the present invention that the manufacturing of the composite can occur essentially at low temperatures, such as between 5 and 37° C., preferably at room temperature. Hence, the manufacturing process supports the inclusion of proteins and proteinaceous growth factors such as morphogenetic proteins in the solutions, suspensions and slurries of the present invention, and hence in the ready composite.

It should be noted that the various uses of the material of the present invention include general surgical applications in bone repair, as well as applications in dental surgery.

Characteristics and properties of a porous calcium phosphate ceramic that are of importance to its osteoinductive properties are:

- dimension of the nanocrystals (the crystals of the calcium phosphate are preferably as long as possible, and may suitably have a length of about 100 nm-10 μm, such as 100-800 nm, preferably about 200-600 nm, more preferably about 300-400 nm, and a width of about 20-200 nm, more preferably about 40-150 nm, most preferably about 80 nm);
- micropore size (the mean diameter of at least 10 of the largest micropores as visible in SEM micrographs, upon magnification and inspection of a surface area of the material of approximately 10-20 μm×5-15 μm);
- area percentage of micropores (e.g. the number of pixels in a digital image associated with micropores as a percentage of the total number of pixels of the selected surface area: the area percentage of micropores in sectional view of the material);
- protein adsorption (e.g the amount of protein absorbed by a volume of 1 ml of porous ceramic when soaked in 3 ml of a 1% fetal bovine serum (FBS) solution in 25 ppm $NaN_3$ after incubation at 37° C. for 24 hrs, and determining the amount absorbed from the amount remaining in solution, using for instance a BCA™ Protein Assay Kit (Pierce Biotechnology Inc., Rockford, Ill., USA), and
- amount of the calcium phosphate nanocrystals.

Materials exhibiting higher bone forming ability have a higher content of calcium phosphate crystals. The 40 CaP composite of Example 3 is an example of such an improved calcium phosphate ceramic. In general, a calcium phosphate ceramic showing much improved osteoinductive properties has a grain (a single crystal or agglomerates of crystals) size smaller than 1.50 μm, (between 0.01-1.50 μm). area percentage of micropores on calcium phosphate ceramic surface higher than 10% (between 10-40%) and higher protein adsorption which is equivalent to more than 40% protein (between 40-80%) from 3 ml 1% foetal bovine serum solution into 1.0 ml (or approximately 400 mg) porous ceramic particles (having total porosity of 80%) in 24 hrs.

It has further been found that the osteoinductivity of calcium phosphate materials may be considerably improved by providing the calcium phosphate material with an effective amount of trace elements, which trace elements are then released over time from the material. In essence, the material must be capable of release of the trace elements for the osteoinductive capacity to be effectively improved. Therefore a very suitable calcium phosphate material and one that inherently exhibits the ability for release of trace elements is a resorbable calcium phosphate material, because such a material is capable of releasing trace elements comprised therein while it is being degraded and resorbed. The trace element is selected from the group consisting of water soluble salts of F, Si, Cu, Li, Al, Mg, Mn, Zn, Ge, Sr and combinations thereof. More preferably the trace element is a water soluble salt of F and/or Li, most preferably the sodium salt of F and/or chloride salt of Li. The effective amount of a trace element depends both on the trace element and on the calcium phosphate used. For instance in the case of sodium fluoride (NaF) and TCP, an effective amount is in the range of 8-24 mmol, NaF/100 g with an optimum around 16 mmol NaF/100 g TCP. Therefore, a preferred range for NaF in the case of TCP is 10-22, more preferably 12-20, still more preferably 14-18, still more preferably 15-17, and most preferably around 16 mmol NaF/100 g TCP. While for LiCl, an effective amount is in the range of 5-45 mmol, LiCl/100 g with an optimum around 15 mmol LiCl/100 g TCP. Therefore, a preferred range for LiCl in the case of TCP is 10-22, more preferably 12-20 mmol/100 g.

Preferably, the trace elements are mixed into the calcium phosphate compound during preparation thereof or are admixed tot the mixture of calcium phosphate and polymer in the ball mill.

It should be taken into account that the toxicity of trace elements depends on the concentration in the body or in parts thereof. Therefore, the effective amount that can be comprised in a calcium phosphate material before it becomes toxic depends in many cases on the rate of release and thus on the stability of the calcium phosphate matrix in the body. Less stable calcium phosphate matrices will degrade more rapidly, releasing larger amounts of trace elements per unit of time and can hold lower effective amounts of trace elements than do more stable matrices. An advantage in the case of ceramics, comprising ratios of compounds with different stability, is that the stability of the ceramic can be varied by varying the amounts of the various compounds. This allows for adjustment of the desired release-rates of trace elements from the calcium phosphate material.

The invention will now be illustrated by way of the following non-limiting examples.

EXAMPLES

Example 1

Synthesis of Nano-Sized Apatite

Preparation of the Solutions for the Nano-Apatite Precipitation
 a. Dissolve 235 g $Ca(NO_3)_2 \cdot 4H_2O$ in 2 liters of distilled water (solution A) (about 0.5M);
 b. Dissolve 78.9 g $(NH_4)_2HPO_4$ in 1.25 liters of distilled water (solution B) (0.5M);
 c. Add 400 ml of ammonia in 1.35 liters of distilled water (solution C) in the next step, with these solutions, a total volume of ±5 liters of solution will be obtained.

Apatite Slurry Synthesis
 a. Assemble a reaction circuit composed of peristaltic pumps, stirrer/heater with control system for the temperature and glass Erlenmeyers
 b. Increase the temperature of the solution A up to 80° C., stirring it at about 500 rpm
 c. Add the solution B to the solution A at the speed of 12.5 ml/min, and in the same time add the solution C to the solution A at the speed of 17.5 ml/min
 d. After that solutions B and C are finished, keep the system under stirred conditions for 2 more hours at 80° C.

Room Temperature Aging
 Age the final solution at room temperature overnight, without stirring Suspension in Distilled Water
 Refresh the supernatant with distilled water several times (till the smell of ammonia disappears), and suspend the apatite slurry in water Filter to Get the Apatite Cake
 Filter the slurry using a vacuum pump and a paper filter, then move the cakes in a glass bottle Suspension of the Apatite Cakes (the Slurry) in Acetone
 Move the cakes into a glass bottle and add 200 ml of acetone, let it stir for at least 2 hours at about 250 rpm, at room temperature. After 2 hours-stirring, stop the stirrer and wait that the apatite nanocrystals precipitate on the bottom of the bottle, then throw away the supernatant, add again 200 ml of fresh acetone and stir (250 rpm) at room temperature for 2 more hours. Repeat these operations 5 times, every two hours.

Figure 1:
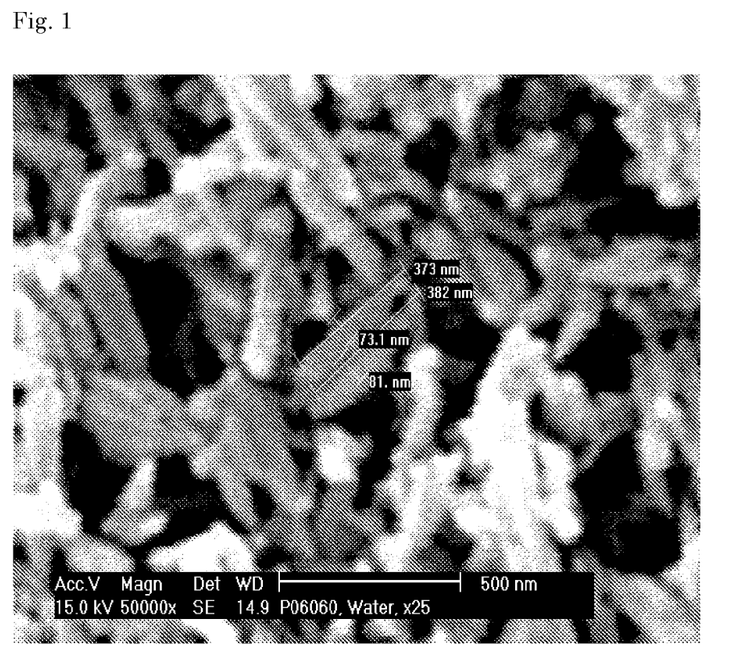
FIG. 1 Measurement of calcium phosphate nanocrystals.

The suspension of nano-apatite in acetone is now ready for use to prepare nano-composites with solvent methods or acetone is evaporated to get dry calcium phosphate nanocrystals for preparation of nanocomposites with melting intrusion method. The resulting crystals of the apatite have average dimensions of 84±19 (width)×369±41 nm (length) (see FIG. 1).

Example 2

Production of Nanocomposites

Figure 2:
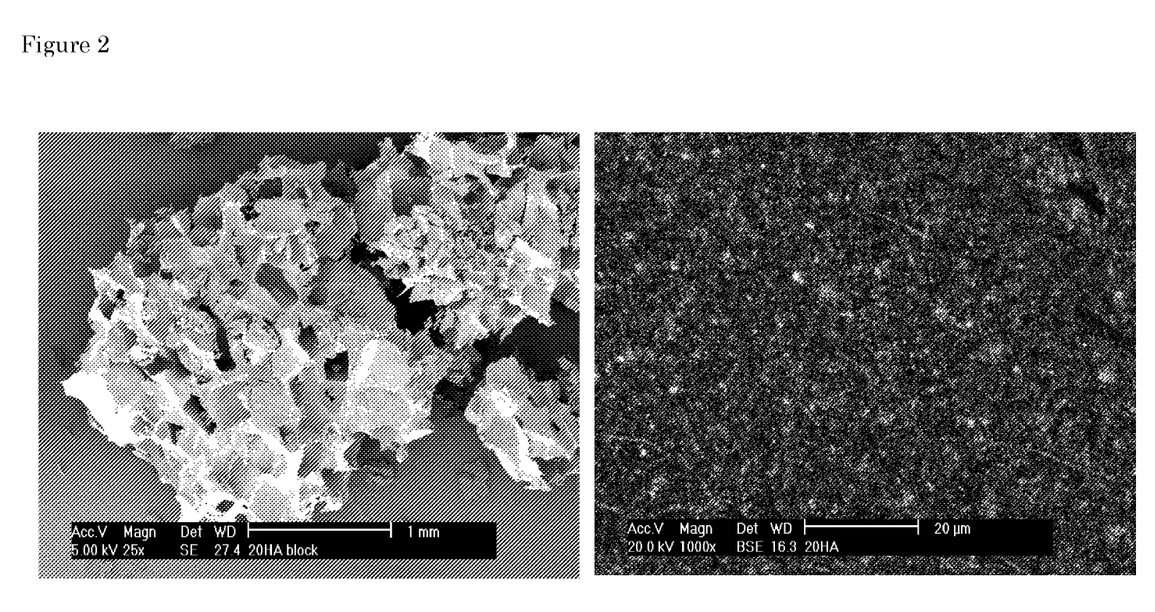
FIG. 2 Left, composite porous particles. Right, BSEM image showing the distribution of apatite nanocrystals in the polymer
FIG. 3 Overview of the stained sections after 12 weeks implantation. As it can be seen, the bone formation occurred only in 40CaP composites. The arrows indicate the formed bone.

Acetone, the nano-apatite/acetone suspension of Example 1, acetone/polylactide solution (PLA) and a porogenic agent, NaCl particles of 300-400 µm, were blended with a rotational ball mill system by using glass beads (diameter ranging between 3-10 mm) at room temperature. The glass balls loading volume represented ⅓ of the whole volume of the ball mill chamber. The rotation speed of the system was 12 rpm. After evaporation of acetone and leaching of NaCl with distilled water porous bodies were obtained. Both porous blocks (dimensions 7×7×7 mm, porosity 60%) and particles (size 1-3 mm) were made and sterilized with gamma irradiation with doses ranging between 28.9 kGy and 30.7 kGy. Backscattered electron microscopic examination showed that the nano-apatite crystals were uniformly distributed in the polymer matrix (FIG. 2).

Example 3

Osteoinducing Capabilities of the Nanocomposites

Using the method of Example 2, four composites with varying apatite content were prepared: 0, 10, 20 and 40% (w/v). Composites in discs (n=3 per apatite content) were soaked in a simulated body fluid (SBF) at 37±1° C. At different time points of 1, 2, 4, 7 and 14 days, the composites were observed with SEM with respect to apatite formation on their surface. No apatite layer was formed in 0 CaP, 10 CaP, and 20 CaP at time points up to 14 days, but an apatite layer was formed in 40 CaP at day 2.

Cultured human bone marrow stromal cells (HBMSC) were, after the $2^{nd}$ passage, seeded onto discs at a cell density of 20,000 cells/disc and cultures for 4 days. Cells attached and grew on the materials with and without CaP. No clear difference was observed in the composites on the basis of the different CaP contents.

Figure 3:
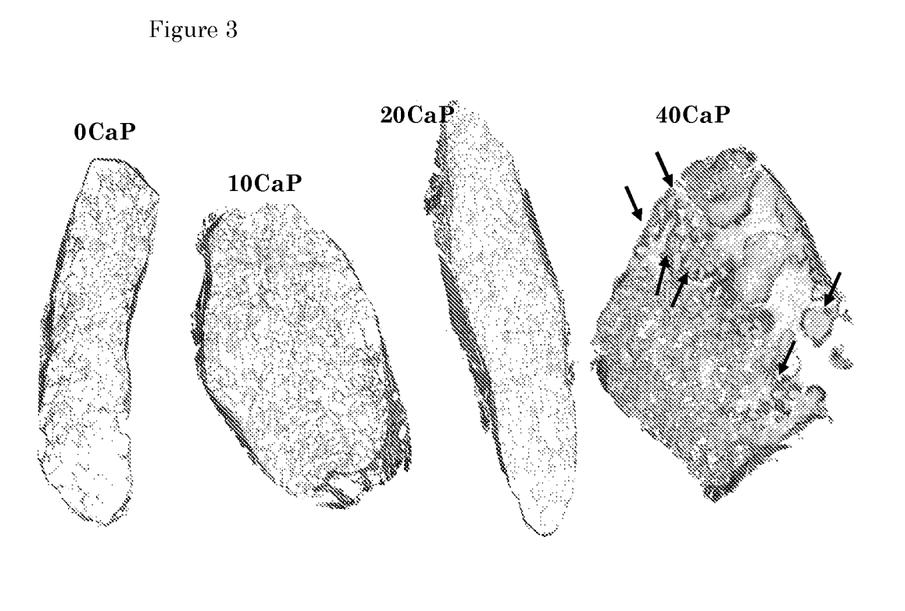
Figure 4:
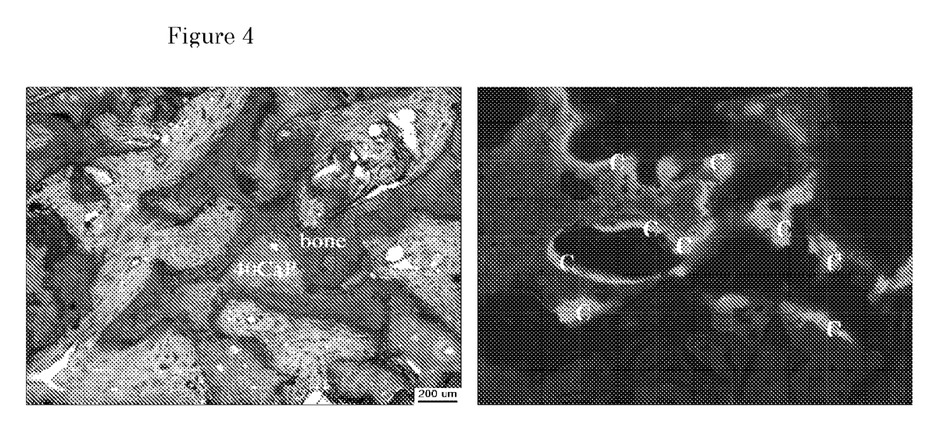
FIG. 4 Left, bone induction in 40CaP after 12 weeks of intramuscular implantation. Right, fluorescent image showing that bone formation started between 6 and 9 weeks after implantation (C, calcein).

Porous blocks (7×7×7 mm, n=7 per material) were implanted in paraspinal muscle of 7 dogs for 12 weeks. Tetracycline, xylenol orange and calcein were intravenously injected 3, 6 and 9 weeks after implantation, respectively. Harvested samples were fixed in 4% buffered formaldehyde at 4° C. for 1 week, dehydrated with a series of ethanol solutions (70%, 80%, 90%, 95% and 100% per 2 times each, 3 days each step) and embedded in methylmetacrylate and non-decalcified histological sections (10-20 µm) were made. Sections for light microscopic observations were stained with 1% methylene blue and 0.3% basic fuchsin solutions, while unstained sections were used for fluorescent microscopic evaluations. At retrieval the implants were surrounded by a layer of connective tissue and a limited inflammatory reaction was observed. All implants of 0 CaP, 10 CaP and 20CaP collapsed and lost porous structures, 40 CaP retained its shape and the pores were filled with de novo bone tissue (n=7, which was directly formed on the material surface (FIG. 3). In other material (0 CaP, 10 CaP, 20 CaP no bone formation was detected. Histomorphological results are summarized in Table 1. Fluorescence microscopy showed that bone formation in 40 CaP started between 6 and 9 weeks after implantation (FIG. 4). The 40 CaP implants retained their shape, while the other implants lost their shape and porous architecture. Moreover, from histological images it was observed that the material degrades, and that mechanical strength increased with apatite content, since 40 CaP kept its shape for 12 weeks.

TABLE 1

Bone incidence and newly formed bone percentage in pores after 12 weeks of implantation in 7 dogs.

| Material | Incidence | % bone in pores |
|---|---|---|
| 0 CaP | 0/7 | 0 |
| 10 CaP | 0/7 | 0 |
| 20 CaP | 0/7 | 0 |
| 40 CaP | 7/7 | 4.9 ± 4.46 |

The invention claimed is:

1. A porous osteoinductive composite material comprising a biocompatible polymer, at least 20 wt.% by weight of the total composition of calcium phosphate nanocrystals, wherein said calcium phosphate nanocrystals are non-heated and non-sintered amorphous non-stoichiometric calcium phosphate crystals, wherein said calcium phosphate nanocrystals have needle-shaped or plate-shaped crystals having a width of about 5-200 nm, said composite having a porosity of at least 10% and having pores with a pore size of at least 50 µm.

2. The material according to claim 1, wherein said calcium phosphate nanocrystals have needle-shaped or plate-shaped crystals having a width of about 10-150 nm.

3. The material according claim 1, wherein said calcium phosphate nanocrystals are present in said material in an amount of at least 40 wt. %.

4. The material according to claim 1, wherein said porosity is 30 to 70% and wherein said pore size is 100 to 1000µm.

5. A method for preparing the osteoinductive composite material according to claim 1, comprising the steps of:
   a) adding phosphate to a calcium solution thereby evoking precipitation of calcium phosphate nanocrystals wherein said calcium phosphate nanocrystals have needle-shaped or plate-like crystals having a width of about 5-200 nm;
   b) washing the calcium phosphate nanocrystals with water and either suspending the nanocrystals in an organic solvent to provide a suspension of calcium phosphate nanocrystals and/or drying said calcium phosphate nanocrystals by evaporating said organic solvent to provide powder of dried calcium phosphate nanocrystals;
   c) providing a polymer in the form of a polymer solution wherein said polymer is dissolved in an organic solvent capable of dissolving said polymer or providing a meltable polymer in the form of a dry powder;
   d) mixing the calcium phosphate nanocrystals of step b) with the polymer provided in step c), in order to provide a composite material mixture;
   e) adding a porogenic agent to said composite material mixture and continue mixing to provide a composite material mixture with porogenic agent, in the form of a melt prepared by melting intrusion of the dry components or in the form of a solution prepared by mixing the dissolved and/or suspended components;

f) moulding the composite material mixture with porogenic agent by pouring the said composite material mixture with porogenic agent into a mould and evaporating the organic solvent, or by cooling said melt of said composite material mixture with porogenic agent and allowing it to set, thereby providing a moulded composite material mixture with porogenic agent;

g) leaching the porogenic agent from the said moulded composite material mixture with porogenic agent by contacting said porogenic agent with a solvent to obtain the osteoinductive composite material.

6. The method according to claim 5, wherein the calcium phosphate nanocrystals are prepared using a calcium solution comprising no more than 0.5 M of Ca, and a phosphate solution comprising no more than 0.5 M of P at a reaction rate equivalent to the production of 1 gram of nanocrystals per minute.

7. The method according to claim 5, wherein the dry calcium phosphate nanocrystals are obtained through dehydration with organic agents, selected from acetone or ethanol, and introduced into the polymer by melting intrusion.

8. The method according to claim 5, wherein the polymer in step c) is dissolved in the same organic solvent as used for the calcium phosphate in step b).

9. The method according to claim 5, wherein said porogenic agent is in the form of particles selected from the group consisting of salts NaCl, KCl, $CaCl_2$, sodium tartrate, and sodium citrate; biocompatible mono- and disaccharides glucose, fructose, dextrose, maltose, lactose, and sucrose; polysaccharides starch, alginate, and pectin; and water soluble proteins gelatine and agarose.

10. The method according to claim 5, wherein the organic solvent is chosen from the group consisting of ethanol, ethyl formate, hexafluoro-2-propanol (HFIP), cyclic ethers, acetone, acetates of C2 to C5 alcohol, glyme or dimethoxyethane, methylethyl ketone, dipropyleneglycol methyl ether, lactones, 1,4-dioxane, 1,3-dioxolane, ethylene carbonate, dimethylcarbonate, diethylcarbonate, benzene, toluene, benzyl alcohol, p-xylene, N-methyl-2-pyrrolidone, dimethylformamide, chloroform, 1,2-dichloromethane (DCM), morpholine, dimethylsulfoxide (DMSO), hexafluoroacetone sesquihydrate (HFAS), anisole and mixtures thereof.

11. The method according to claim 5, wherein the organic solvent is acetone.

12. The method according to claim 5, wherein the polymer is chosen from the group consisting of polyesters, polyanhydrides, polyamides, polyurethanes, polyesteramides, polyorthoesters, polydioxanones, polyacetals, polyketals, polycarbonates, polyphosphazenes, polyhydroxybutyrates, polyhydroxyvalerates, polyalkylee oxalates, polyalkylene succinates, poly(malic acid), poly(amino acids), poly(methylvinyl ether), poly(maleic anhydride), polyvinyl alcohol, and copolymers, terpolymers, natural cellulose polymers, chitosan, alginate, collagen, chitin, glycogen, starch, keratins, polypepetides or combinations or mixtures thereof.

13. The method according to claim 12, wherein the polymer is chosen from polylactide (PLA), polycaprolactone (PCL or copolymers thereof.

14. The method according to claim 5, wherein the calcium phosphate is in the form of amorphous non-stoichiometric calcium phosphate nano-crystals with Ca/P ratio of 1.0-2.0.

15. A method for the induction of bone formation in a living organism, comprising the steps of
a) providing the osteoinductive composite material according to claim 1; and
b) implanting said material in a living organism in need thereof.

16. A method for the production of autologous bone in a non-osseous site, comprising the steps of
a) providing the osteoinductive composite material according to claim 1; and
b) implanting said material alone or combined with growth factors or/and cells in a non-osseous site.

17. The method according to claim 16 wherein said material is implanted during dental surgery.

18. The method according to claim 16 wherein said material is implanted for the reconstruction of bone.

19. The material according to claim 2, wherein said calcium phosphate nanocrystals have needle-shaped or plate-shaped crystals having a length of up to 10 μm.

* * * * *